US008415513B2

(12) United States Patent
Oren et al.

(10) Patent No.: US 8,415,513 B2
(45) Date of Patent: *Apr. 9, 2013

(54) CONTINUOUS PROCESS OF PREPARING BROMOPICRIN (75) Inventors: Jakob Oren, Nesher (IL); Nasif Yassin, Tamra (IL); Ron Frim, Haifa (IL)

(73) Assignee: Bromine Compounds Ltd., Beer-Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/601,547

(22) PCT Filed: May 26, 2008

(86) PCT No.: PCT/IL2008/000712
§ 371 (c)(1),
(2), (4) Date: Nov. 24, 2009

(87) PCT Pub. No.: WO2008/146277
PCT Pub. Date: Dec. 4, 2008

(65) Prior Publication Data
US 2010/0204528 A1    Aug. 12, 2010

(30) Foreign Application Priority Data
May 27, 2007    (IL) .......................... 183445

(51) Int. Cl.
C07C 205/00    (2006.01)
(52) U.S. Cl. .................................... 568/946
(58) Field of Classification Search ................. 568/946
See application file for complete search history.

(56) References Cited

U.S. PATENT DOCUMENTS

| 2,763,962 | A | 9/1956 | Hardy |
| 2,895,869 | A | 7/1959 | Bluestone |
| 2,916,855 | A | 12/1959 | Thiegs |
| 3,159,686 | A | 12/1964 | Burk et al. |
| 3,261,742 | A | 7/1966 | Kishikawa et al. |
| 3,445,576 | A | 5/1969 | Kenaga et al. |
| 3,929,723 | A | 12/1975 | Freedman et al. |
| 4,039,731 | A | 8/1977 | Freedman et al. |
| 4,053,633 | A | 10/1977 | Goralski et al. |
| 4,078,089 | A | 3/1978 | Levek et al. |
| 4,922,030 | A | 5/1990 | Nocito et al. |
| 5,013,762 | A | 5/1991 | Smith et al. |
| 5,043,489 | A | 8/1991 | Nocito et al. |
| 5,144,087 | A | 9/1992 | Williams et al. |
| 5,397,804 | A | 3/1995 | Hirashima et al. |
| 5,411,990 | A | 5/1995 | Tsuji et al. |
| 2007/0249501 | A1 | 10/2007 | Frim et al. |
| 2010/0152501 | A1 | 6/2010 | Oren et al. |

FOREIGN PATENT DOCUMENTS

| AU | 2005312894 | 6/2006 |
| CN | 1903830 | 1/2007 |
| EP | 0206173 | 12/1986 |
| EP | 0398795 | 1/1990 |
| EP | 0364789 | 4/1990 |
| JP | 42-012772 | 7/1967 |
| JP | 42-014815 | 8/1967 |
| JP | 06-293710 | 10/1994 |
| JP | 09-067212 | 3/1997 |
| JP | 2002-088005 | 3/2002 |
| JP | 2003-012573 | 1/2003 |
| JP | 2003-104951 | 4/2003 |
| WO | WO 94/01391 | 1/1994 |
| WO | WO 2006/061842 | 6/2006 |
| WO | WO 2007/023496 | 3/2007 |
| WO | WO 2007/023496 A2 * | 3/2007 |
| WO | WO 2008/146277 | 12/2008 |

OTHER PUBLICATIONS

Response Dated Apr. 13, 2011 to Examination Report of Apr. 23, 2010 From the Intellectual Property Office of New Zealand Re.: Application No. 584731.
Office Action Dated Oct. 27, 2010 From the Israel Patent Office Re. Application No. 183821 and Its Translation Into English.
Examination Report Dated Apr. 23, 2010 From the Intellectual Property Office of New Zealand Re.: Application No. 556062.
Official Action Dated May 3, 2010 From the US Patent and Trademark Office Re.: U.S. Appl. No. 11/989,585.
Response Dated May 23, 2010 to Office Action of Jan. 22, 2010 From the State Intellectual Property Office of the People's Republic of China Re.: Application No. 200580047583.2.
Response Dated Sep. 20, 2011 to Examination Report of Jun. 21, 2011 From the Intellectual Property Office of New Zealand Re.: Application No. 584731.
Response Dated Nov. 18, 2010 to Official Action of Jul. 20, 2010 From the US Patent and Trademark Office Re.: U.S. Appl. No. 11/808,492.
Response Dated Nov. 28, 2010 to Examination Report of Apr. 23, 2010 From the Intellectual Property Office of New Zealand Re.: Application No. 556062.
Translation of Office Action Dated Oct. 27, 2010 From the State Intellectual Property Office of the People's Republic of China Re. Application No. 200680030435.4.
Translation of Notice of Reason for Rejection Dated Dec. 16, 2011 From the Japanese Patent Office Re. Application No. 2008-527594.
Notice of Allowance Dated Jan. 21, 2011 From the US Patent and Trademark Office Re.: U.S. Appl. No. 11/989,585.
Response Dated Feb. 24, 2011 to Office Action of Oct. 27, 2010 From the Israel Patent Office Re. Application No. 183821.

(Continued)

Primary Examiner — Jafar Parsa (57) ABSTRACT

A continuous process of preparing bromopicrin is disclosed. The process is effected by transferring a continuous flow of a first mixture and a continuous flow of a second mixture into a first reactor, the first mixture containing nitromethane and bromine and the second mixture containing an aqueous solution of an alkaline substance, to thereby obtain a reaction mixture which comprises bromopicrin in said first reactor; and collecting the bromopicrin from the reaction mixture. Highly pure bromopicrin obtained by this process is also disclosed.

27 Claims, 4 Drawing Sheets

OTHER PUBLICATIONS

Response Dated Feb. 27, 2011 to Office Action of Oct. 27, 2010 From the State Intellectual Property Office of the People's Republic of China Re. Application No. 200680030435.4.
Response Dated Apr. 13, 2011 to Examiner's Report of Apr. 23, 2010 From the Australian Government, IP Australia Re. Application No. 2005312894.
Official Action Dated Apr. 22, 2010 From the US Patent and Trademark Office Re.: U.S. Appl. No. 11/808,492.
Examiner's Report Dated May 16, 2011 From the Australian Government, IP Australia Re. Application No. 2005312894.
Examination Report Dated Apr. 23, 2010 From the Intellectual Property Office of New Zealand Re.: Application No. 584731.
Examination Report Dated Jun. 10, 2011 From the Intellectual Property Office of New Zealand Re. : Application No. 584731.
Official Action Dated Jul. 20, 2010 From the US Patent and Trademark Office Re.: U.S. Appl. No. 11/808,492.
Response Dated Jun. 16, 2011 to Official Action of Mar. 29, 2011 From the Ministry of Education and Science, Department of Intellectual Property of Ukraine Re.: Application No. 200803490.
Response Dated May 31, 2011 to the Examination Report of Apr. 23, 2010 From the Intellectual Property Office of New Zealand Re.: Application No. 584731.
Examination Report Dated Nov. 2, 2011 From the State Enterprise Ukrainian Institute of Industrial Property, State Department of Intellectual Property of Ukraine Re. Application No. a 200913580 and Its Summary in English.
Response Dated Dec. 20, 2011 to Examination Report of Nov. 2, 2011 From the State Enterprise Ukrainian Institute of Industrial Property, State Department of Intellectual Property of Ukraine Re. Application No. a 200913580.
Response Dated Dec. 21, 2011 to Examination Report of Dec. 1, 2011 From the Intellectual Property Office of New Zealand Re.: Application No. 584731.
Response Dated Dec. 27, 2011 to Notice of Reasons for Rejection of Oct. 14, 2011 From the Japanese Patent Office Re. Application No. 2007-545110.
Translation of Notice of Reasons for Rejection Dated Oct. 14, 2011 From the Japanese Patent Office Re. Application No. 2007-545110.
Response Dated Jan. 12, 2011 to Official Action of Oct. 14, 2010 From the US Patent and Trademark Office Re.: U.S. Appl. No. 11/989,585.
Official Action Dated Jan. 19, 2011 From the US Patent and Trademark Office Re.: U.S. Appl. No. 11/808,492.
Official Action Dated Mar. 29, 2011 From the Ministry of Education and Science, Department of Intellectual Property of Ukraine Re.: Application No. 200803490 and Its Translation Into English.
Response Dated May 26, 2011 to Official Action of Mar. 29, 2011 From the Ministry of Education and Science, Department of Intellectual Property of Ukraine Re.: Application No. 200803490.
Response Dated Jul. 20, 2011 to Examination Report of Jun. 21, 2011 From the Intellectual Property Office of New Zealand Re.: Application No. 584731.
Response Dated Jul. 21, 2011 to Examiner's Report of May 16, 2011 From the Australian Government, IP Australia Re. Application No. 2005312894.
Response Dated Jul. 22, 2011 to Examiner's Report of May 16, 2011 From the Australian Government, IP Australia Re. Application No. 2005312894.
Response Dated Jul. 31, 2011 to Office Action of Mar. 29, 2011 From the Israel Patent Office Re. Application No. 183445.
Response Dated Jul. 31, 2011 to Office Action of Mar. 29, 2011 From the Israel Patent Office Re. Application No. 189687.
Official Action Dated Oct. 14, 2010 From the US Patent and Trademark Office Re.: U.S. Appl. No. 11/989,585.
Response Dated Apr. 17, 2011 to Official Action of Jan. 19, 2011 From the US Patent and Trademark Office Re.: U.S. Appl. No. 11/808,492.
Translation of Office Action Dated Nov. 25, 2011 From the State Intellectual Property Office of the People's Republic of China Re.: Application No. 200580047583.2.

Examination Report Dated Dec. 1, 2011 From the Intellectual Property Office of New Zealand Re.: Application No. 584731.
Office Action Dated Mar. 29, 2011 From the Israel Patent Office Re. Application No. 183445 and Its Translation Into English.
Office Action Dated Mar. 29, 2011 From the Israel Patent Office Re. Application No. 189687 and Its Translation Into English.
Official Action Dated Jun. 7, 2010 From the Ministry of Education and Science, Department of Intellectual Property of Ukraine Re.: Application No. 200803490 and Its Translation Into English.
Response Dated Aug. 2, 2010 to Official Action Dated Jun. 7, 2010 From the Ministry of Education and Science, Department of Intellectual Property of Ukraine Re.: Application No. 200803490.
Response Dated Aug. 3, 2010 to Official Action of May 3, 2010 From the US Patent and Trademark Office Re.: U.S. Appl. No. 11/989,585.
Examination Report Dated May 4, 2012 From the Instituto Mexicano de la Propriedad Industrial Re. Application No. MX/a/2007/006932 and Its Translation Into English.
Translation of Office Action Dated Mar. 9, 2012 From the State Intellectual Property Office of the People's Republic of China Re. Application No. 200680030435.4.
Office Action Dated Mar. 29, 2012 From the Israel Patent Office Re. Application No. 183821 and Its Translation Into English.
Translation of Notice of Reasons for Rejection Dated May 8, 2012 From the Japanese Patent Office Re. Application No. 2007-545110.
Communication Pursuant to Rules 70(2) and 70a(2) EPC Dated Jul. 23, 2012 From the European Patent Office Re. Application No. 05838189.8.
Examination Report Dated Aug. 8, 2012 From the Instituto Mexicano de la Propriedad Industrial Re. Application No. MX/a/2007/006932 and Its Translation Into English.
Office Action Dated Aug. 9, 2012 From the Israel Patent Office Re. Application No. 183445 and Its Translation Into English.
Supplementary European Search Report and the European Search Opinion Dated Jul. 4, 2012 From the European Patent Office Re. Application No. 05838189.8.
Bartoshevich et al. "Structure and Antimicrobial Properties of Certain Bromonitro Compounds", Pharmaceutical Chemistry Journal, XP055030445, 6: 11-13, 1972.
Clark et al. "Synthesis and Antimicrobial Activity of Aliphatic Nitro Compounds", Journal of Medicinal Chemistry, XP055030443, 17(9): 977-981, Sep. 1, 1974.
Fridman et al. "[Synthesis and Study of the Physiological Activity of Aliphatic Nitro Compounds. X. Realation Among Structure, Toxicity, and Micromicrobial Activity in a Series of Nitroalkanes and Their Alpha-Halo Derivatives]", Khimiko-Farmatsevticheskii Zhurnal, XP009160009, 10(6): 53-56, Jan. 1976. Russian Only. p. 54-55, Table.
Malatesta et al. "Sull'Attivit? Antibatterica di Alcuni Alogeni-Derivati Alifatici e in Particolare Della Cloro e Bromopicrina. Contributo Allo Studio Del Loro Meccanismo di Azione [Antibacterial Action of Some Aliphatic Halogen Compounds, Especially of Bromopicrin]", Il Farmaco, Scienza e Technica, XP009160006, 6(2): 137-141, Mar.-Apr. 1951.
Zsolnai "Tribrom-Nitromethan—ein hochwirksames Desinfienz [Tribrom-Nitromethan—A New Disinfectant of High Efficiency]", Zentralblatt f?r Bakteriologie, Parasitenkunde, Infektionskrankheiten und Hygiene, 1. Abteilung, Originale Reihe A, Medizinische Mikrobiologie und Parasitologie, XP009160007, 224(4): 496-502, Jan. 1, 1973. p. 498, Table 1, p. 501.
International Preliminary Report on Patentability Dated Mar. 6, 2008 From the International Bureau of WIPO Re.: Application No. PCT/IL2006/000978.
International Preliminary Report on Patentability Dated Jun. 21, 2007 From the International Bureau of WIPO Re.: Application No. PCT/IL2005/001330.
Examination Report Dated Jun. 5, 2009 From the Intellectual Property Office of New Zealand Re.: Application No. 556062.
International Search Report and the Written Opinion Dated Aug. 2, 2006 From the International Searching Authority Re.: Application No. PCT/IL05/01330.
International Search Report Dated Oct. 15, 2008 From the International Searching Authority Re.: Application No. PCT/IL2008/000712.

International Search Report Dated May 16, 2007 From the International Searching Authority Re.: Application No. PCT/IL06/00978.
Response Date Oct. 18, 2009 to Office Action of Aug. 6, 2009 From the State Intellectual Property Office of the People's Republic of China Re.: Application No. 200580047583.2.
Supplementary European Search Report and European Search Opinion Dated Oct. 15, 2008 From the European Patent Office Re.: Application No. 06796066.6.
Translation of Notice of Division of Application Dated Aug. 6, 2009 From the State Intellectual Property Office of the People's Republic of China Re.: Application No. 200580047583.2.
Written Opinion Dated Oct. 15, 2008 From the International Searching Authority Re.: Application No. PCT/IL2008/000712.
Writen Opinion Dated May 16, 2007 From the International Searching Authority Re.: Application No. PCT/IL06/00978.
Juby et al. "The Origin of Carbon Atoms 2, 3, and 7 of Ricinine", Canadian Journal of Chemistry, XP002498043, 41: 117-122, 1963. p. 117. Compound VIII.
International Preliminary Report on Patentability Dated Dec. 1, 2009 From the International Bureau of WIPO Re.: Application No. OPCT/IL2008/000712.
Official Action Dated Dec. 14, 2009 From the US Patent and Trademark Office Re.: U.S. Appl. No. 11/808,492.
Response Dated Jan. 14, 2010 to Official Action of Dec. 14, 2009 From the US Patent and Trademark Office Re.: U.S. Appl. No. 11/808,492.
Response Dated Feb. 16, 2010 to Official Action of Aug. 18, 2009 From the Ministry of Education and Science. Department of Intellectual Property of Ukraine Re.: Application No. 200803490.
Response Dated Mar. 17, 2010 to Examination Report Jun. 5, 2009 From the Intellectual Property Office of New Zealand Re.: Application No. 556062.
Translation of Office Action Dated Jan. 22, 2010 From the State Intellectual Property Office of the People's Republic of China Re.: Application No. 200580047583.2.
Translation of Office Action Dated May 21, 2012 From the State Intellectual Property Office of the People's Republic of China Re. Application No. 200880100846.5.
Examiner's Report Dated Apr. 23, 2010 From the Australian Government, IP Australia Re. Application No. 2005312894.
Response Dated May 24, 2010 to Official Action of Apr. 22, 2010 From the US Patent and Trademark Office Re.: U.S. Appl. No. 11/808,492.
Examination Report Dated Jun. 21, 2011 From the Intellectual Property Office of New Zealand Re.: Application No. 584731.

* cited by examiner

CONTINUOUS PROCESS OF PREPARING BROMOPICRIN

RELATED APPLICATIONS

This application is a National Phase of PCT Patent Application No. PCT/IL2008/000712 having International filing date of May 26, 2008, which claims the benefit of Israel Patent Application No. 183445 filed on May 27, 2007. The contents of the above Applications are all incorporated herein by reference.

FIELD AND BACKGROUND OF THE INVENTION

The present invention relates to the field of chemical synthesis and manufacturing, and more particularly, to a continuous process of preparing bromopicrin, and highly pure bromopicrin produced therefrom.

Bromopicrin (CAS Registry No. 464-10-8), synonymously known as 1,1,1-tribromonitromethane (methane, tribromonitro-), nitrotribromomethane (methane, nitrotribromo-), and nitrobromoform, has a chemical formula of $CBr_3NO_2$, a molecular weight of 297.728 grams/mol, a melting point of 10° C., a boiling point of 89-90° C. (at 20 mm Hg), a specific gravity of 2.79, water solubility of about 1.5 grams per liter water (at 20° C.), and appears either as prismatic crystals in the solid phase, or as an oily colorless liquid.

Bromopicrin belongs to the general chemical family of halonitroalkanes (or equivalently, nitrohaloalkanes), which includes, for example, mono-, di-, and tri-, bromonitroalkanes and mono-, di-, and tri-, chloronitroalkanes, such as mono-, di-, and tri-, bromonitromethanes and mono-, di-, and tri-, chloronitromethanes, respectively.

Selected examples of bromonitromethanes, such as bromopicrin, and uses thereof, are disclosed in U.S. Pat. No. 5,866,511, to Dallmier, et al.; U.S. Pat. No. 5,591,759, to Ito, et al., U.S. Pat. Nos. 5,411,990, and 5,397,804, each to Tsuji, et al.; U.S. Pat. No. 5,013,762, to Smith, et al.; and U.S. Pat. Nos. 4,039,731; 4,020,249; 4,017,666; and 3,968,096, each to Freedman, et al.

WO 2006/061842, by the present assignee, teaches novel pesticide formulations of bromopicrin and methods of using same for disinfecting substances, products or structures and particularly for controlling plant pests.

It is worthy to note that in none of these disclosures was there any mention of the purity or source of the bromonitromethane, in particular of bromopicrin, let alone an indication of the synthesis or manufacturing of the bromonitromethane.

Selected examples of bromopicrin used as a consumable reactant or ingredient in processes of preparing another composition or formulation are provided in the disclosures of U.S. Pat. Nos. 5,219,938, 5,128,416, 5,015,692, and 4,957,976, but none of these disclosures describes a process of preparing bromopicrin, nor of its purity level. In U.S. Pat. No. 4,922,030, another bromonitromethane, monobromonitromethane, is custom synthesized for the subsequent preparation of monobromonitroalcohol.

In general, methods or processes of synthesizing and/or manufacturing halonitroalkanes are well known and described, for example, in Tscherniak, in Ann. 180, 128-130 (1876); U.S. Pat. No. 2,309,806, to Tindall; U.S. Pat. No. 2,633,776, to Slagh; U.S. Pat. No. 4,922,030, to Nocito, et al.; U.S. Pat. No. 5,043,489, to Nocito, et al.; and U.S. Pat. No. 5,180,859, to Timberlake, et al.

Since bromopicrin is a halonitroalkane, one might expect that these processes will be applicable in the preparation of bromopicrin. However, it turns out that bromopicrin and dibromonitromethane are only described therein in the context of undesirable polyhalogenated nitromethane low-yield by-products or impurities of the desired monobromonitromethane product. Hence, in none of the above disclosures is there a description of a method of preparing pure bromopicrin as the target product in high yield.

Preparation of Bromopicrin by the Distillation of an Aqueous Mixture of Picric Acid, calcium hydroxide, and bromine, was first disclosed by Stenhouse, in Annalen 91, 307 (1854). It is also known that bromopicrin can be prepared by a reaction of picric acid with a basic metal hypobromite, wherein the bromopicrin product is isolated in high yield by distillation.

These processes suffer several significant disadvantages and limitations, as follows:

a) picric acid is potentially explosive under even mild conditions, and therefore, using picric acid as a reactant involves working at potentially hazardous conditions.

b) bromopicrin is a highly energetic compound, having a relatively high exothermic heat of decomposition (HOD), whereby about 1700 Joules/gram are released during its decomposition. Thus, bromopicrin is potentially hazardous under certain conditions, for example during its recovery and purification from the reaction mixture by distillation.

c) even when using solvent extraction instead of distillation for recovering and purifying bromopicrin from the reaction product, then an extraction procedure needs to be incorporated into the overall method, thereby introducing an organic solvent into an otherwise organic solvent-free method, which would add additional costs, health hazards, and organic solvent waste management, to the overall method.

d) this process is inapplicable as a large volume industrial sized process, due to the high cost of scaling up the bromopicrin recovery and purification stages.

WO 2007/023496, by the present assignee, filed Aug. 22, 2006, discloses for the first time a novel batch process for the preparation of bromopicrin which does not use picric acid as a starting material, thus overcoming the above detailed drawbacks. The process taught in WO 2007/023496 is based on a reaction of bromine, nitromethane (NM) and an alkaline substance, as depicted by the following 'generalized' chemical equation (aq.=aqueous):

Nitromethane+bromine+alkaline substance (aq.)→ bromopicrin+$H_2O$+secondary products (organic phase) (aqueous phase)

In an exemplary preferred embodiment of this process, the alkaline substance is a metal alkali base, such as sodium hydroxide or potassium hydroxide.

As taught in WO 2007/023496 the process is effected by first obtaining a mixture of nitromethane and bromine, preferably in the presence of water and without adding any organic solvent. Then, the alkaline substance is added in portions to the mixture and rapidly and selectively reacts with the bromine contained in the nitromethane mixture, and forms one or more bromine-containing chemical intermediate(s), which in turn, selectively react(s) with the already present nitromethane, thus selectively forming the desired high purity bromopicrin product in high yield. Once the reaction is completed, the heavier (lower) organic phase, containing the bromopicrin, is separated from the lighter (upper) aqueous phase, and bromopicrin is thus collected from the reaction mixture.

According to the teachings of WO 2007/023496 the recommended reaction conditions for the preparation of bromopicrin were determined to be:

Temperature in the reactor: 40° C. (±5)
$Br_2$/Nitromethane molar ratio: 3.25 (±0.03)
Concentration of aqueous NaOH: 35% by weight (±1)
Reaction time (time of addition of base): 4-6 hours Under these conditions, the selectivity of the reaction is more than 96%, even more than 99%, and the yield is high: e.g., between 92% and 94.5% (based on nitromethane). The selectivity and yield of the process depend on the temperature of the reaction ($T_R$), the molar ratio between the bromine and the nitromethane and the time period during which the base is added. In this respect, it was determined that the formation of the impurities could be prevented by using a sufficiently high starting $Br_2$:nitromethane molar ratio (for example, about 3.25).

Thus, the process disclosed in WO 2007/023496, overcomes the disadvantages of previously-known methods for the preparation of bromopicrin from picric acid, while obtaining a high yield and high quality bromopicrin product.

As known in the design of industrial chemical processes, process reactors are defined as either batch or continuous processors, based upon the mode in which they handle samples or product for processing. Batch process reactors are the simplest mode of reactor operation. In this mode, the process reactor is loaded with medium and the reaction is allowed to proceed. When the reaction is completed, the contents are emptied for downstream processing. The reactor is then cleaned, re-filled, re-inoculated and the reaction process starts again.

In continuous process reactors, fresh media is continuously added and reactor fluid (containing waste as well as desired products) is continuously removed. The reactor can thus be operated for long periods of time without having to be shut down. Continuous process reactors can be many times more productive than batch reactors and are generally the preferred mode in industrial processing, being more time- and cost-effective.

To date, no continuous process has been described for the preparation of bromopicrin from nitromethane and bromine, in the presence of a base.

SUMMARY OF THE INVENTION

The present inventors have now designed and successfully practiced a novel process of preparing bromopicrin. By being operated in a continuous mode, this process is industrially applicable, reproducible, safe, environmentally friendly, and cost effective, and hence can be beneficially used for producing large amounts of high purity bromopicrin.

According to one aspect of the present invention there is provided a process of preparing bromopicrin, the process comprising:

transferring a continuous flow of a first mixture and a continuous flow of a second mixture into a first reactor, the first mixture containing nitromethane and bromine and the second mixture containing an aqueous solution of an alkaline substance, to thereby obtain a reaction mixture which comprises bromopicrin in the first reactor; and collecting the bromopicrin from the reaction mixture, thereby preparing bromopicrin.

According to some embodiments of the invention described below, the first mixture and the second mixture are transferred, via said continuous flow, into the first reactor simultaneously.

According to some embodiments the process is performed such that the reaction mixture is substantially absent of an organic solvent.

According to some embodiments the first mixture is prepared by mixing nitromethane and bromine at a temperature that ranges from about 10° C. to about 50° C. Preferably, the temperature ranges from about 20° C. to about 25° C.

According to some embodiments, a molar ratio of the bromine and the nitromethane in the first mixture ranges from about 3 to about 4.

According to some embodiments the ratio ranges from about 3 to about 3.1.

According to some embodiments, the alkaline substance is selected from the group consisting of metal alkali hydroxides, alkaline earth hydroxides, and combinations thereof.

According to some embodiments the metal alkali hydroxide is selected from the group consisting of lithium hydroxide, sodium hydroxide, potassium hydroxide and combinations thereof.

According to some embodiments the metal alkali hydroxide is selected from the group consisting of sodium hydroxide, potassium hydroxide and a combination thereof.

According to some embodiments the alkaline substance is sodium hydroxide.

According to some embodiments a concentration of the alkaline substance in the aqueous solution of the second mixture ranges from about 5 weight percents to about 40 weight percents of the total weight of the aqueous solution weight.

According to some embodiments a concentration of the alkaline substance in the aqueous solution of the second mixture ranges from about 20 weight percents to about 35 weight percents of the total weight of the aqueous solution weight.

According to some embodiments the concentration ranges from about 26 weight percents to about 27 weight percents of the total weight of the aqueous solution weight.

According to some embodiments a residence time of the reaction mixture in the first reactor ranges from about 0.3 hours to about 6 hours, preferably from about 0.5 hours to about 4 hours.

According to some embodiments the first reactor is maintained at a temperature that ranges from about 30° C. to about 100° C., preferably from about 40° C. to about 80° C.

According to some embodiments the process described herein, further comprises, prior to collecting the bromopicrin, transferring the reaction mixture from the first reactor to a second reactor.

According to some embodiments the second reactor is maintained at a temperature that ranges from about 15° C. to about 30° C., preferably from about 20° C. to about 25° C.

According to some embodiments the process described hereinabove, further comprises, prior to collecting the bromopicrin, cooling the reaction mixture.

According to some embodiments the process described hereinabove, further comprises, subsequent to collecting the bromopicrin, collecting an aqueous phase from the reaction mixture.

According to some embodiments the process described hereinabove, further comprises, chemically treating said aqueous phase, to thereby provide a treated form of the aqueous phase. In some embodiments, chemically treating the aqueous phase comprises regeneration of bromine and/or sodium bromide.

According to some embodiments the bromopicrin is obtained in a chemical yield equal to or higher than 90 weight percents, preferably equal to or higher than 95 weight percents, more preferably equal to or higher than 98 weight percents, all relative to nitromethane.

According to some embodiments the bromopicrin has a purity equal to or higher than 99 weight percents.

According to another aspect of the present invention there is provided bromopicrin, prepared by any of the processes described hereinabove.

According to some embodiments of the invention described below, the bromopicrin has a purity equal to or greater than 99 weight percents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein, the term "about" refers to ±10%.

BRIEF DESCRIPTION OF THE DRAWINGS

The present invention is herein described, by way of example only, with reference to the accompanying drawings. With specific reference now to the drawings in detail, it is stressed that the particulars shown are by way of example and for purposes of illustrative description of the preferred embodiments of the present invention only, and are presented in the cause of providing what is believed to be the most useful and readily understood description of the principles and conceptual aspects of the present invention. In this regard, no attempt is made to show structural details of the present invention in more detail than is necessary for a fundamental understanding of the invention, the description taken with the drawings making apparent to those skilled in the art how the several forms of the invention may be embodied in practice. In the drawings.

DESCRIPTION OF THE PREFERRED EMBODIMENTS

The present invention is of a novel process of preparing bromopicrin, and of high purity bromopicrin produced thereby. Specifically, the present invention, in some embodiments thereof, is of a continuous process of preparing bromopicrin, which is based on transferring a continuous flow of an aqueous solution of an alkaline substance, for example, a metal alkali base such as sodium hydroxide, and a continuous flow of a mixture of nitromethane and bromine, preferably free of organic solvents, into a reactor, and thereafter collecting the organic phase containing the bromopicrin directly, in particular, via gravity, from the reaction mixture, without subjecting the organic phase to distillation or extraction. The present invention, in some embodiments thereof, is further of bromopicrin having a purity equal to or greater than 99 percent, and a yield higher than 95 percents, and even higher than 98 percents (based on nitromethane), obtained by this process.

The principles and operation of the process according to the present embodiments may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As discussed in detail hereinabove, bromopicrin is a halonitroalkane which is known as an environmentally-safe and effective agricultural agent and has been suggested as a replacement for environmentally-problematic antimicrobial, biocidal, and antiseptic agents, such as methyl bromide, 1,3-dichloropropene, methyl isothiocyanates, methyl iodide (iodomethane) and propargyl bromide.

Although methods of preparing halonitroalkanes are well known and described, they are mostly not applicable in the preparation of bromopicrin. The available high-yield process for preparing bromopicrin was, until recently, distillation of an aqueous mixture of picric acid, calcium hydroxide, and bromine (Stenhouse (1854) supra) or a reaction of picric acid with a basic metal hypobromite, followed by distillation. This process is disadvantageous due to the explosive nature of the picric acid and the hazardous nature of the bromopicrin under distillation. Furthermore, an introduction of organic solvents may be necessary in order to avoid distillation, thereby adding additional costs, health hazards, and organic solvent waste management, to the overall method. All this becomes even more complicated if scaling up is needed, for the production of large quantities of bromopicrin.

As discussed in detail hereinabove, recently, a novel batch process for the preparation of bromopicrin, based on a reaction of bromine, nitromethane (NM) and an alkaline substance has been disclosed in WO 2007/023496, by the present assignee (supra). This process is a batch-type process and is further based on a batch-wise addition of the alkaline substance, performed such that no excess of the alkaline substance is present in the reaction mixture.

Figure 1:
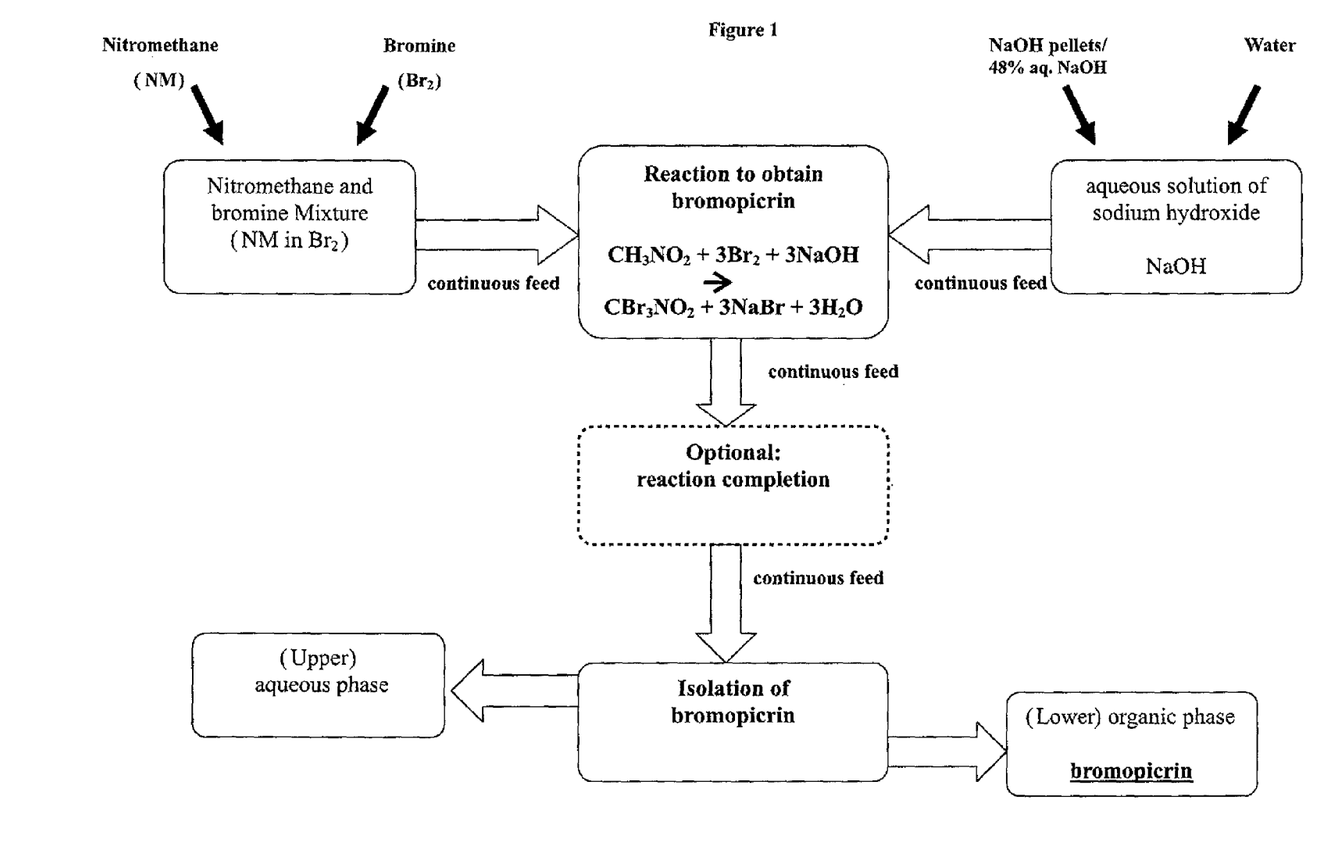
FIG. 1 is a flow block diagram of a general scheme of implementing the present embodiments, using reactors operated in a continuous mode for manufacturing bromopicrin.

While further exploring the process of preparing bromopicrin, the present inventors have now designed and successfully practiced a continuous process for the preparation of bromopicrin, which is based on transferring a continuous flow of each of a nitromethane/bromine mixture and an aqueous alkaline substance solution into a reactor, as depicted for example in FIG. 1.

Thus, as demonstrated in the Examples section that follows, using a highly advantageous, cost-effective and time-consuming continuous process, bromopicrin is obtained in a high purity (greater than 99%), a high yield (over 95% and even 98%, based on nitromethane) and at extremely high throughputs (between 220 and 1000 grams/hour/liter reactor), which render this process highly applicable for the industrial production of large quantities of bromopicrin.

This continuous process is further advantageously characterized by being performed at such conditions in which formation of undesired products is avoided, thus circumventing the need to control parameters such as temperature and pH.

The term "purity" defines the weight percent of the desired compound, of the total weight of the product.

The term "yield" defines the ratio between practical consumption and theoretical consumption of nitromethane.

Thus, according to dome of the present embodiments there is provided a process of preparing bromopicrin. The process is effected by transferring a continuous flow of a first mixture, containing nitromethane and bromine, and a continuous flow of a second mixture, containing an aqueous solution of an alkaline substance, into a first reactor, so as to obtain therein a reaction mixture which comprises bromopicrin; and collecting the bromopicrin from the reaction mixture.

The term "flow", as used herein and in the art, refers to a continuous progression or streaming, of either a liquid or a gas material.

The term "continuous flow" or "continuous process", as used herein, refers to a process that is effected without the need to be intermittently stopped or slowed.

The term "transferring", as used herein, refers to the mobilization of reactants and/or reaction mixture from one vessel and/or reactor to another, which can be performed manually or mechanically, e.g., via pipes or by using calibrated or non-calibrated pumps (e.g., peristaltic pumps). The term "transferring" is also referred to herein and in the art as "feeding", with respect to the vessel and/or reactor to which reactants and/or a reaction mixture are transferred.

The first mixture is a mixture of nitromethane and bromine, which is preferably prepared in a separate reactor by simply mixing the bromine and the nitromethane.

The mixing of the bromine and the nitromethane in this separate reactor is preferably effected by stirring, for example, by using an automatically controllable mechanical or electro-mechanical stirrer.

Although the (initial) temperature of the mixture of nitromethane and bromine can be varied, in general the (initial) temperature of the mixture of nitromethane and bromine, is in a range of, preferably, between about 10° C. and about 50° C., and more preferably, between about 20° C. and about 25° C. (corresponding to room temperature).

The overall process of preparing bromopicrin, according to the present invention, is summarized in equation [1] hereinbelow. According to this equation, the stoichiometric ratio between the bromine and the nitromethane is 3:1.

$$CH_3NO_2 + 3Br_2 + 3NaOH\ (aq.) \rightarrow CBr_3NO_2 + 3NaBr + 3H_2O + \text{secondary products (organic phase)(aqueous phase)} \quad [1]$$

In practice, as taught in WO 2007/023496, supra, a higher than stoichiometric ratio is often needed in order to obtain a desirable yield and purity. Thus, the bromine and the nitromethane ratio can be any ratio above 3:1, with typical values being 3.3:1 and 3.25:1.

It has now been surprisingly found that the continuous process described herein can be effected at high yield and purity even when the bromine:nitromethane ratio is as low as 3.1:1 or even 3:1, in average being about 3.07:1 (see, Table 1 hereinunder). Using lower amounts of bromine, at nearly stoichiometric ratios, is evidently highly advantageous in terms of cost, safety, environmental considerations, etc.

The mixture of nitromethane and bromine is preferably prepared without adding any organic solvent to the mixture, so that it is substantially free of organic solvents. This aspect is evidently advantageous in that additional costs, health hazards, and organic solvent waste management are avoided.

The second mixture is an aqueous solution of an alkaline substance.

The term "aqueous solution" is used to include either water or an aqueous mixture of water and an organic solvent, the latter being optionally added. Preferably, the aqueous solution comprises water and is devoid of an organic solvent, as delineated hereinabove.

This alkaline substance is essentially any type of alkaline material which is capable of rapidly and selectively reacting with the bromine (while in the presence of water and nitromethane), for forming one or more bromine-containing chemical intermediate(s), for example, a metal hypobromite formed by reaction between a metal alkali hydroxide, such as sodium hydroxide or potassium hydroxide and bromine, as generally indicated by chemical equation [2]:

$$Br_2 + \text{alkaline substance (aq.)} \rightarrow [\text{Br-chemical intermediate(s)}] + H_2O\ [\text{rapid and selective}] \quad [2]$$

For example, two equivalents of sodium hydroxide (NaOH) react with bromine ($Br_2$), so as to produce sodium hypobromite (NaOBr, 1 equivalent), sodium bromide (NaBr, 1 equivalent) and water ($H_2O$, 1 equivalent).

In turn, the one or more bromine-containing intermediate(s), in the presence of water, selectively react(s) with the already present nitromethane, for selectively forming the desired high purity bromopicrin product in high (essentially, theoretical stoichiometric) yield, as generally indicated by chemical equation [3]:

NaOH+secondary products (organic phase)
(aqueous phase)    [3]

Without being bound to any particular mechanism, it is assumed that the hypobromite reacts with nitromethane, so as to produce bromonitromethane and sodium hydroxide. The bromonitromethane then reacts with the constantly produced hypobromite, so as to produce dibromonitromethane, which then similarly reacts so as to produce tribromonitromethane (bromopicrin).

For example, the alkaline substance is selected from the group consisting of metal alkali hydroxides, alkaline earth hydroxides, and combinations thereof. Exemplary metal alkali hydroxides are lithium hydroxide [LiOH], sodium hydroxide [NaOH], and potassium hydroxide [KOH]. Exemplary alkaline earth hydroxides are magnesium hydroxide [$Mg(OH)_2$], calcium hydroxide [$Ca(OH)_2$], strontium hydroxide [$Sr(OH)_2$], and barium hydroxide [$Ba(OH)_2$].

For performing this procedure, preferably, the alkaline substance is a metal alkali hydroxide selected from the group consisting of lithium hydroxide [LiOH], sodium hydroxide [NaOH], potassium hydroxide [KOH], and a combination thereof. In some embodiments, the alkaline substance is a metal alkali hydroxide selected from the group consisting of sodium hydroxide [NaOH], potassium hydroxide [KOH], and a combination thereof. In some embodiments, the alkaline substance is sodium hydroxide [NaOH].

Sodium hydroxide is preferred over potassium hydroxide for performing this procedure, mainly based on chemical process economics. For comparable quality (purity), and concentration, sodium hydroxide costs less than potassium hydroxide.

As can be seen in the Examples section which follows, sodium hydroxide was used in the samples prepared hereinbelow, while maintaining high yield, high purity and high throughput of bromopicrin.

Thus, according to an embodiment of the present invention, the alkaline substance is sodium hydroxide.

The concentration of the alkaline substance within the aqueous solution can be expressed in units of, for example, percent (weight/weight) or (w/w), corresponding to the percent of the weight ratio of the alkaline substance within the aqueous solution.

In general, the concentration of the alkaline substance in the aqueous solution of the alkaline substance can be varied, but it is often used at a concentration which ranges from about 5 weight percents to about 40 weight percents of the total weight of the aqueous solution weight.

As can be seen in the Examples section which follows, in all of the tested samples (Table 1), the concentration of the alkaline substance within the aqueous solution was lower than 35 weight percents, generally in the range of from about 26 weight percents to about 27 weight percents.

Thus, according to some embodiments of the present invention, the concentration of the alkaline substance in the aqueous solution of the second mixture ranges from about 20 weight percent to about 35 weight percent of the total weight of the aqueous solution weight and, more preferably, is approximately 26 or 27 weight percents.

The first mixture and the second mixture described herein are preferably prepared and used in a batch mode type of a chemical reactor, but can also be prepared and used in a continuous mode type of a chemical reactor.

In general, essentially any batch mode type of chemical reactor can be used as the chemical reactor for preparing the nitromethane and bromine mixture or the alkaline substance aqueous solution. In some embodiments, the chemical reactor is operatively constructed or fitted with equipment, for example, a temperature controllable chemical reactor jacket, for enabling manual, semi-automatic, or fully automatic temperature control of the contents inside the chemical reactor, for pre-determined ranges of temperature, for example, with a capability of setting the temperature inside the chemical reactor within an overall range of between about 10° C. and 50° C. In such an embodiment, preferably, the temperature controllable equipment is operatively connected to a manual, semi-automatic, or fully automatic, respectively, temperature controller, for example, a Lauda automatic chemical reactor temperature controller device operative with variable chemical reactor temperature set point, which, in turn, is operatively connected to an appropriate power supply. Additionally, preferably, the chemical reactor is operatively constructed or fitted with equipment, for example, a mechanical or electromechanical stirrer, for enabling manual, semi-automatic, or fully automatic mixing or stirring control of the contents of the chemical reactor, for pre-determined ranges of mixing or stirring speed, and for pre-determined patterns or configurations of mixing or stirring. In such an embodiment, preferably, the mixing or stirring controllable equipment is operatively connected to a manual, semi-automatic, or fully automatic, respectively, mixing or stirring controller, which, in turn, is operatively connected to an appropriate power supply.

In some embodiments of the present invention, the continuous flow of the first mixture and the continuous flow of the second mixture are transferred into the first reactor simultaneously.

As taught in WO 2007/023496 (supra), which describes a batch process for the preparation of bromopicrin, the absence of excess alkaline substance (e.g., NaOH) in the reaction mixture containing bromopicrin is essential to prevent any possible undesirable reaction between the excess alkaline substance and the bromopicrin.

Thus, in a batch-type process, the concentration of the alkaline substance in the reaction mixture is determined by adding this substance portion-wise, so as to avoid formation of an excess thereof.

In a continuous process, the addition rates of each of the first and second mixtures described herein determines the ratio between the alkaline substance and the bromine at any given moment during the reaction course, and allows performance of the reaction such that no excess alkaline substance (which can adversely react with nitromethane) is present and hence the alkaline substance reacts substantially solely with the bromine. The addition rates of the first and the second mixtures described herein therefore determines the reaction selectivity. These addition rates should therefore preferably not exceed the reaction rate.

Thus, the rate of addition of the second mixture (e.g., the NaOH aqueous solution) preferably corresponds with the rate of addition of the first, bromine/nitromethane mixture, and both are preferably equal to or lower than the reaction rate.

Yet further, the rate of addition of the first and/or second mixtures invariably influences the heat formed in the reaction, and are therefore preferably selected such that a reasonable heat is obtained. By "reasonable heat" it is meant that the temperature of the exothermic reaction can be readily controlled by conventional techniques.

The residence time of the obtained reaction mixture is relatively short, and may range, for example, from about 0.3 to 6 hours. In some embodiments, the residence time ranges from about 0.5 hours to about 4 hours. For example, the residence time in all of the experiments presented in Table 1 in the Examples section hereinbelow was lower than 2.5 hours. In one embodiment, the residence time is about 2 hours.

The term "residence time" refers to the average time that the reactants spend in a reactor and is used as a measure of the processing rate for flow reactors. The residence time can be estimated by dividing the volume of a chamber or region by the volumetric flow rate through it. Thus: Residence time=Reactor Volume/Flow Rate, whereby the flow rate is the sum of the flow rates of the first and the second mixtures.

As shown in the Examples section that follows, the process described herein was practiced while varying the overall process time. Thus, overall process times varying from 6 to 30 hours were practiced and were found to not significantly affect the yield or purity of the bromopicrin, thus demonstrating the reproducibility of the process.

In general, essentially any continuous mode type of chemical reactor can be used as the chemical reactor for mixing the nitromethane in bromine mixture with the alkaline substance solution, and has at least two side inlets/outlets. Preferably, the chemical reactor is operatively constructed or fitted with equipment, for example, a temperature controllable chemical reactor jacket, for enabling manual, semi-automatic, or fully automatic temperature control of the contents inside the chemical reactor, for pre-determined ranges of temperature, for example, with capability of setting the temperature inside the chemical reactor within an overall range of between about 10° C. and 50° C. In such an embodiment, preferably, the temperature controllable equipment is operatively connected to a manual, semi-automatic, or fully automatic, respectively, temperature controller, for example, a Lauda automatic chemical reactor temperature controller device operative with variable chemical reactor temperature set point, which, in turn, is operatively connected to an appropriate power supply. Additionally, preferably, the chemical reactor is operatively constructed or fitted with equipment, for example, a mechanical or electro-mechanical stirrer, for enabling manual, semi-automatic, or fully automatic mixing or stirring control of the contents of the chemical reactor, for pre-determined ranges of mixing or stirring speed, and for pre-determined patterns or configurations of mixing or stirring. In such an embodiment, preferably, the mixing or stirring controllable equipment is operatively connected to a manual, semi-automatic, or fully automatic, respectively, mixing or stirring controller, which, in turn, is operatively connected to an appropriate power supply.

Mixing of the reaction mixture in the chemical reactor maximizes contact, and therefore, enhances the reaction between the alkaline substance (e.g., free sodium hydroxide) and the mixture of nitromethane and bromine. Such mixing of the reaction mixture within the chemical reactor also helps to assure that no localized regions or points of the alkaline substance are formed in the chemical reactor, thereby, ensuring that no excess of the alkaline substance occurs in the reaction mixture containing the bromopicrin, thereby decreasing the amount of impurities. Such mixing of the reaction mixture in the chemical reactor also helps to assure uniform heat distribution, throughout the volume of the chemical reactor.

As demonstrated in the Examples section that follows, the reaction starts immediately upon entry of these two streams into the reactor, is fast and provides bromopicrin in high yield (above 98%, relative to nitromethane) and in high purity (>99%).

For performing this process the actual temperature of the reaction (reaction temperature ($T_R$)) and range thereof are maintained at values which depend on several factors. First, the temperature depends on the magnitude and rate of the exothermic heat released during the reaction between the alkaline substance and the mixture of nitromethane and bromine, as generally indicated by chemical equations [2] and [3] above. Then, the temperature also depends on the magnitude and rate of dissipation, transfer, or/and control, of this exothermic heat.

The reaction temperature can also be limited by the physical properties of the reactants and/or intermediates formed during the reaction. Thus, for example, since the boiling point of bromine is 56° C., it may be desirable to maintain the reaction temperature below this temperature.

This requirement, however, is circumvented by performing a continuous process, as described herein, since the bromine that is transferred to the reactor, immediately reacts with the alkaline substance (which is concomitantly transferred to the reactor within the second mixture), so as to form less volatile intermediates. This allows performing the reaction at higher temperatures, which may lead to faster reaction rates and higher yields, and further circumvents the need to maintain the reaction temperature at low temperature by extensive external cooling (due to its exothermic nature).

Thus, according to some embodiments of the present invention, the temperature of the reactor is maintained in a range of between about 30° C. and about 100° C., and preferably, between about 40° C. and about 80° C.

The wider range of reaction temperature in the continuous process enables a faster reaction, contributes to the high throughput and high yield of the reaction and requires less energy to cool the reaction. Hence, conducting the reaction at higher temperatures is advantageous in the preparation of bromopicrin, especially in the preparation of large quantities thereof.

Figure 2:
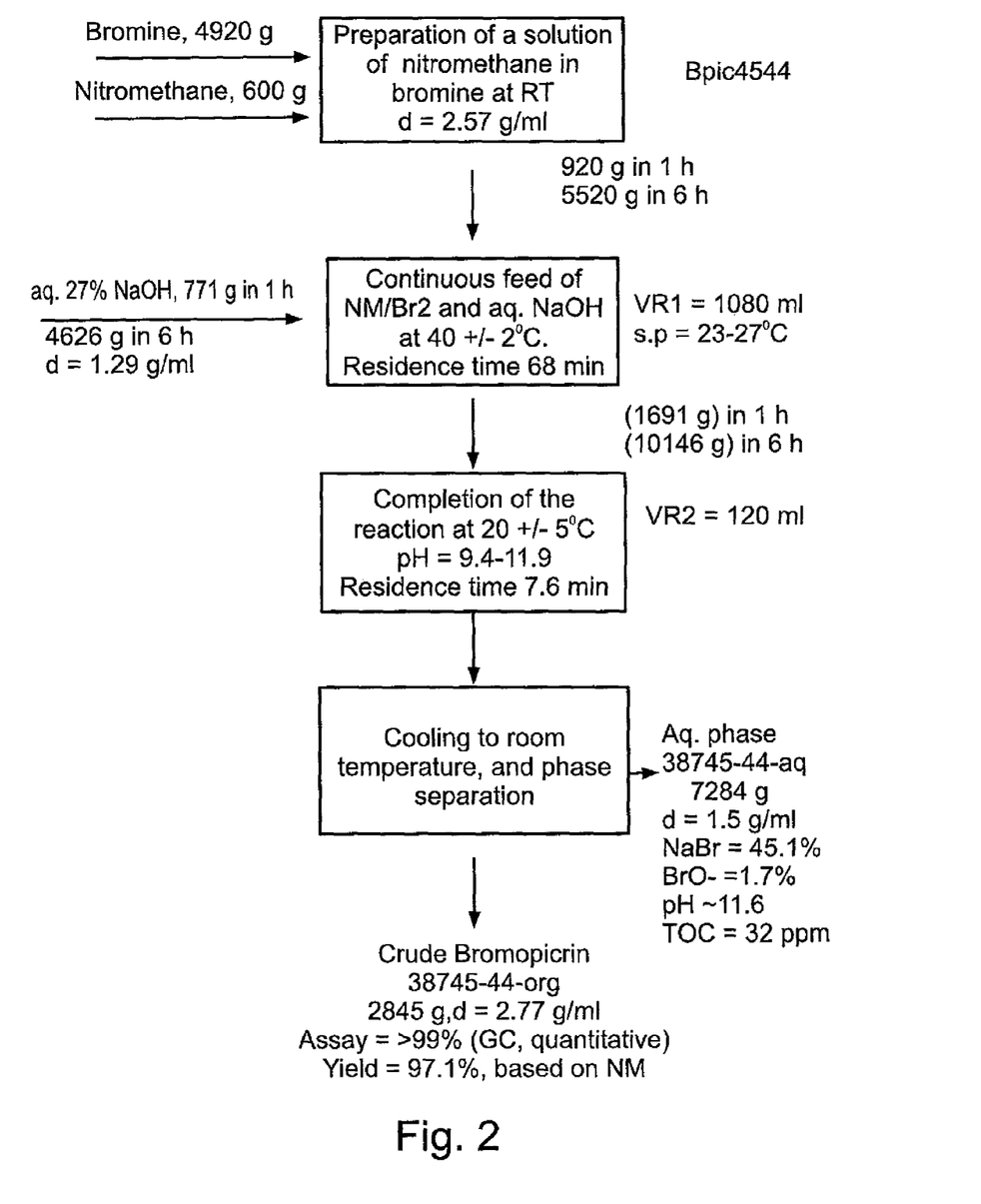
FIG. 2 is a flow block diagram of the actual scheme and procedures of a representative example of implementing some of the present embodiments on a laboratory scale, using a continuous chemical reactor, in which the reaction temperature is 40° C. and the residence time in the reactor is about 68 minutes (overall practiced process time of 6 hours)
Figure 3:
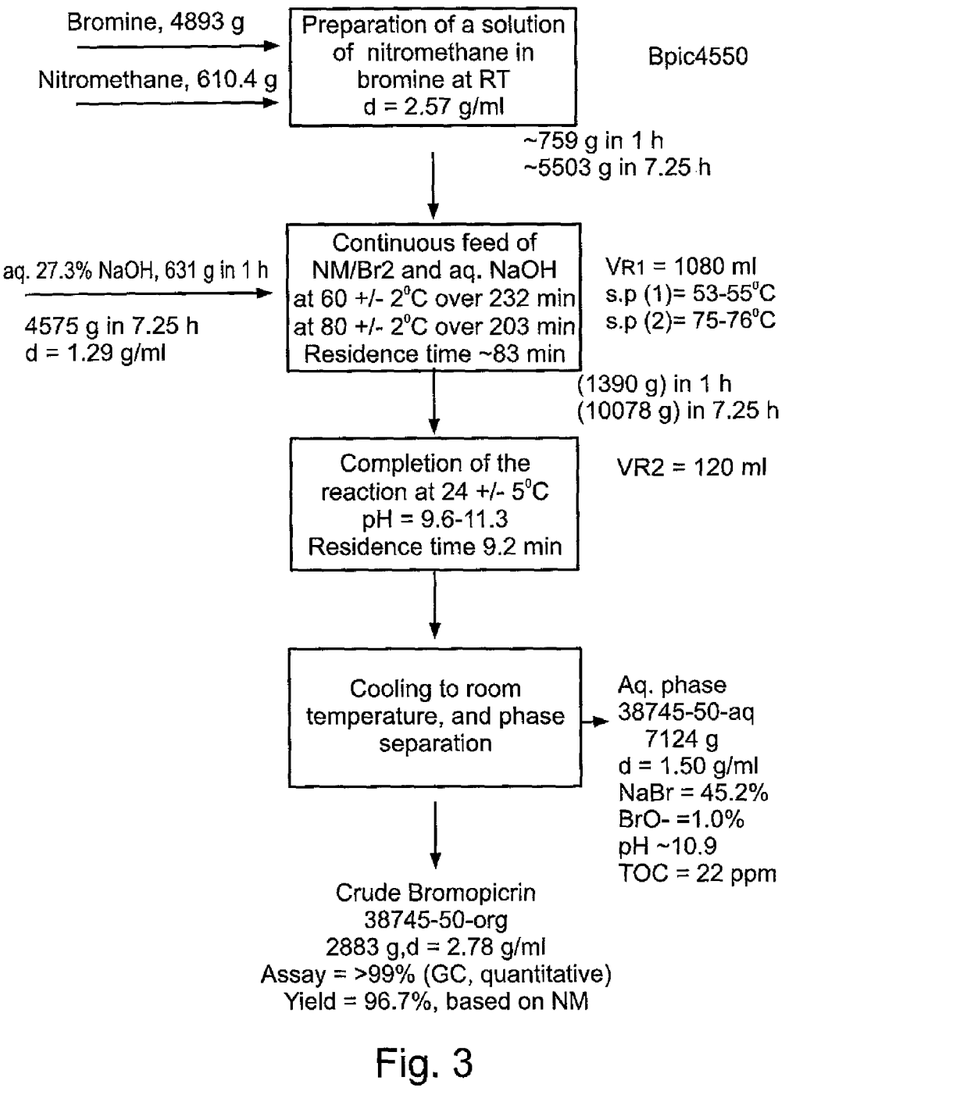
FIG. 3 is a flow block diagram of the actual scheme and procedures of other representative examples of implementing some of the present embodiments on the laboratory scale, using a continuous chemical reactor, in which the reaction temperature is 60° C. or 80° C. and the residence time in the reactor is about 83 minutes (overall practiced process time of 7.25 hours)
Figure 4:
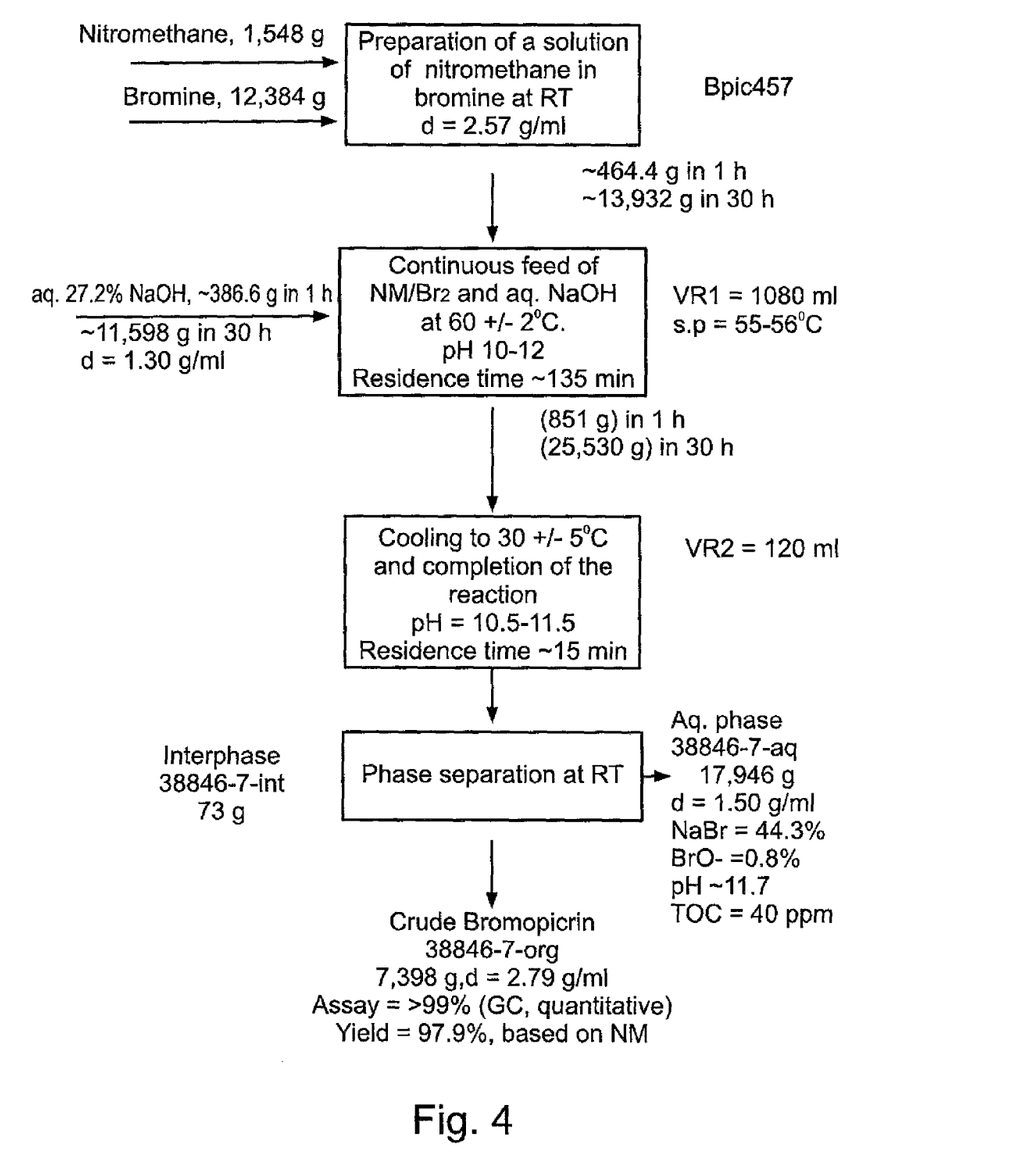
FIG. 4 is a flow block diagram of the actual scheme and procedures of another representative example of implementing some of the present embodiments on the laboratory scale, using a continuous chemical reactor, in which the reaction temperature is 60° C. and the residence time in the reactor is about 135 minutes (overall practiced process time of 30 hours).

In practice, following these considerations, the temperature of the reaction and range thereof, are controlled and maintained at pre-determined values by setting the automatic chemical reactor temperature controller device at a pre-determined set point ("s.p.", as it appears in FIGS. 2-4).

Upon mixing the first and second mixtures in the first reactor, the reaction mixture can, optionally and preferably, be continuously transferred from the first reactor to a second reactor. As discussed in the Examples section that follows, this transfer allows the reactants in the reaction mixture to complete the reaction therebetween. It has been shown that under certain conditions, this transfer greatly improves the yield of the process.

In this case, a reaction mixture which contains bromopicrin, and optionally unreacted reactants and/or intermediates, as delineated hereinabove, overflows into a second reactor, after an almost complete duration of the reaction (reaction time). Thus, the reaction mixture is further mixed in the second chemical reactor, while the temperature of the reaction mixture containing bromopicrin is preferably maintained at room temperature (between about 20° C. and about 25° C.).

The preferred residence time in the second reactor typically depends on the ratio between the size of the first and the second reactors. Thus, for example, considering a 3:1 ratio of the first reactor's size and the second reactor's size, and residence time in the first reactor that ranges from 0.3 hour to 6 hours, a preferred residence time in the second reactor ranges from about 6 minutes to about 120 minutes, preferably, from about 15 minutes to about 80 minutes.

The temperature in the second reactor preferably ranges from about 15° C. to about 30° C., and is more preferably from about 20° C. to about 25° C. (essentially being room temperature).

It has been shown that the pH in the second reactor preferably ranges from about 9 to about 12.5, more preferably from about 10 to about 12.

After the first and optionally the second residence times of the reaction mixture containing bromopicrin, the reaction mixture containing bromopicrin, that is, containing a mixture of primary products: bromopicrin [$CBr_3NO_2$] and water, and secondary products: inorganic salt(s), inorganic oxidant(s), and trace quantities of organic or/and inorganic materials, is allowed to undergo phase separation. The primary product bromopicrin, having a water solubility of about 1.5 grams per liter water at 20° C., and a specific gravity of 2.79, migrates into and became the heavier (lower) organic phase, while the primary product water and the secondary products migrate into and become the lighter (upper) aqueous phase, of the reaction mixture. In a typical example, an aqueous phase formed upon using NaOH as the alkaline substance has a specific gravity of about 1.5.

The heavier (lower) organic phase containing the bromopicrin is selectively collected from the bottom end portion or outlet of the vertically positioned chemical reactor, while initially leaving behind the lighter (upper) aqueous phase (containing water and secondary products) in the chemical reactor. Simultaneously, there can be performed monitoring and measuring at least one property, for example, color, conductivity, or/and density, of the collected liquid, which is accurately and reproducibly characteristic of the collected liquid, that is, the heavier (lower) organic phase containing the bromopicrin, until there appears sign or indication of no more organic phase remaining in the bottom portion of the chemical reactor. This corresponds to the time immediately before the appearance of the first sign or indication of the aqueous phase entering the bottom end portion or outlet of the chemical reactor, at which time the draining or pumping of the heavier (lower) organic phase containing the bromopicrin from the chemical reactor is terminated.

Thereafter, the lighter (upper) aqueous phase (containing water and secondary products), which is initially left behind in the chemical reactor, is collected from the chemical reactor, and is optionally subjected to determination of the chemical composition and make-up of the aqueous phase.

In some embodiments, the phase separation is performed continuously, using any of the respective known methodologies (e.g., by means of a continuous phase separator).

The collected heavier (lower) organic phase (containing bromopicrin) of the reaction mixture can be subjected to the above described gas chromatography chemical analysis procedure, for determining bromopicrin purity and compositions thereof. The collected lighter (upper) aqueous phase (containing water and secondary products) of the reaction mixture can be subjected to standard wet chemistry types of analytical procedures.

The collected aqueous phase can be chemically treated, for example, so as to isolate inorganic salts produced as byproducts in the reaction (e.g., NaBr), and/or so as to re-generate bromine.

The organic phase containing the bromopicrin is directly collected from the reaction mixture, without subjecting the organic phase to distillation or extraction, for obtaining near quantitative (theoretical stoichiometric) yield of bromopicrin having a purity equal to or greater than 99 weight percents. This aspect of the present invention beneficially results in precluding the need for including a distillation or extraction procedure along with relatively expensive distillation or extraction equipment, as well as costs involved for operating and maintaining thereof. This aspect also results in precluding the need for handling and taking into account the effects, in particular, as relating to health and safety, of the potentially hazardous (highly energetic) bromopicrin product during distillation or extraction conditions, as well as of the potentially hazardous and waste generating extraction solvent.

The collected organic phase containing the bromopicrin is hence preferably used 'as is', stored 'as is' in the collection or receiving vessel or container, or transferred to a more suitable storage vessel or container, and then stored in an appropriate chemical storage environment. Suitable storage conditions for bromopicrin are in a low light transmitting container (for example, an opaque brown glass bottle), preferably unexposed to sunlight, at room temperature (that is, between about 20° C. and about 25° C.), and away from potentially flammable or explosive conditions. Under such storage conditions, bromopicrin is relatively stable and remains highly pure for up to at least several months and even for 1 year.

The bromopicrin produced by the process described herein has a purity equal to or greater than 99 weight percents.

Furthermore, the bromopicrin produced by the process described is obtained in a yield higher than 90 weight percents, higher than 95 weight percents, and even higher than 98 weight percents.

As demonstrated in the Examples section that follows, analysis of the aqueous phase showed relatively low impurity levels obtained in the continuous process described herein, further demonstrating the efficacy of this process in terms of yield and purity. For example, the oxidants level was determined to be only 0.4%-2.1% in the continuous process, being in most cases in the range 0.3%-1.7%. Furthermore, the total organic carbon (TOC) values (which reflect the existence of various organic impurities) were also lower: 22-106 ppm (see, Table 2 hereinbelow).

The process described herein is therefore industrially applicable, reproducible, safe, environmentally friendly, and cost effective.

It is to be understood that the present invention is not limited in its application to the details of the order or sequence, and number, of procedures, steps, and sub-steps, of operation or implementation of the process, or to the details of the equipment, reagents, and materials, used for implementing the process, set forth in the following illustrative description, accompanying drawings, and examples, unless otherwise specifically stated herein. The present invention is capable of other embodiments and of being practiced or carried out in various ways. Although procedures, steps, sub-steps, equipment, reagents, and materials, similar or equivalent to those illustratively described herein can be used for practicing or testing the present invention, suitable procedures, steps, sub-steps, equipment, reagents, and materials, are illustratively described herein.

It is also to be understood that all technical and scientific words, terms, and/or phrases, used herein throughout the present disclosure have either the identical or similar meaning as commonly understood by one of ordinary skill in the art to which this invention belongs, unless otherwise specifically defined or stated herein. Phraseology, terminology, and, notation, employed herein throughout the present disclosure are for the purpose of description and should not be regarded as limiting. Moreover, all technical and scientific words, terms, and/or phrases, introduced, defined, described, and/or exemplified, in the above Background section, for example, regarding the synonyms of bromopicrin, are equally or similarly applicable in the illustrative description of the preferred embodiments, examples, and appended claims, of the present invention.

As used herein, the term 'about' refers to ±10 percent of the associated value. Additionally, as used herein, the phrase 'room temperature' refers to a temperature in a range of between about 20° C. and about 25° C.

Procedures, steps, sub-steps, equipment, reagents, and materials, and implementation, of exemplary preferred embodiments, alternative preferred embodiments, specific configurations, and, additional and optional aspects, characteristics, or features, thereof, of the process of preparing bromopicrin, and high purity bromopicrin produced therefrom, according to the present invention, are better understood with reference to the following illustrative description and accompanying drawings. Throughout the following illustrative description and accompanying drawings, same reference numbers, and/or letters, refer to same components.

In the following illustrative description of the process of the present invention, included are main or principal procedures, steps, sub-steps, equipment, reagents, and materials, needed for sufficiently understanding proper 'enabling' utilization and implementation of the disclosed process. Accordingly, description of various possible required and/or optional preliminary, intermediate, minor, procedures, steps, sub-steps, equipment, reagents, and/or materials, of secondary importance with respect to enabling implementation of the invention, which are readily known by one of ordinary skill in the art, and/or which are available in the prior art and technical literature relating to chemical synthesis and manufacturing, are at most only briefly indicated herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Experimental Methods

Chemical Reagents:
Nitromethane [$CH_3NO_2$], in the liquid phase, was obtained from Aldrich (assay of at least 96 weight percent).
Sodium hydroxide [NaOH] aqueous solution (48%) was obtained from F&C, Israel.
Bromine [$Br_2$], in the liquid phase, with an assay of at least 99 weight percent, was obtained from Dead Sea Bromine (DSB), Israel.
Equipment Set-Up:
The nitromethane and bromine mixture, as well as the aqueous NaOH solution were prepared in 2 or 10 liter measuring cylinders, with ground-glass neck, which served as batch-mode feeding reactors.

A calibrated peristaltic pump was used for feeding both the nitromethane/$Br_2$ mixture and the aqueous NaOH solution. Since it is known that Viton® is not resistant to nitromethane, the nitromethane/$Br_2$ feeding tube is made of Teflon®, apart from a small part, between the pump wheels, which is made of Viton®. The NaOH feeding tube is made of Viton®.

Two types of vertically positioned chemical reactors were used to construct a system operative in a continuous mode:
(i) a laboratory scale 1080 ml sized chemical reactor, jacketed and operatively fitted with a mechanical stirrer (set at about 400 RPM), a condenser and a thermocouple; The reactants are introduced into the reactor via tubes in two separate openings. The reactor has a side outlet.
(ii) a four-necked round-bottom 120-ml sized flask with a side outlet, equipped with a mechanical stirrer, condenser, pH meter and thermocouple. Optionally, the reaction mixture passes from reactor (i), into this flask, by overflowing, and goes to completion in this flask, while being cooled to room temperature.

In addition, two 1 liter separating funnels, acting as phase separators are connected to the chemical reactor (the first chemical reactor or, preferably, the second chemical reactor, if present). One funnel is connected to the outlet of the round-bottom flask and receives the reaction mixture continuously while phase separation takes place in the other funnel. After removing the product and the aqueous phase from the second separating funnel, the first funnel is reconnected to the outlet of the round-bottom flask and the second funnel is connected, such that the first funnel repeatedly awaits phase separation. The product (organic phase) is collected in a brown bottle for weighing and analysis, while the aqueous solution is collected in a polyethylene flask for weighing, analysis and further treatment.

A Lauda automatic chemical reactor temperature controller device was connected to each of the reactors (i) and (ii), operative with variable chemical reactor temperature set point (s.p.), which, in turn, was operatively connected to an appropriate power supply.

Analytical Procedures:
Gas Chromatography (GC):
GC analyses were performed on a HP 5890 gas chromatograph, equipped with a RTx-1, capillary column, 15 m×0.25 mm×0.25μ, 100% dimethylpolysiloxane packing, and operated under the following conditions:
Temperature Program (BPK method): Initial temperature of 30° C., 2 minutes; 30° C. to 220° C. at 10° C./minute; 220° C., 5 minutes.
Injector: 170° C.
Detector: 325° C.
Split ratio: 1:100.
Injection amounts: 0.2-0.5 μl (neat). Column retention times of the components were as follows: nitromethane: 2.8 minutes; monobromonitromethane: 4.5 minutes; dibromonitromethane: 6.3 minutes; bromopicrin: 12.3 minutes; and tetrabromodinitroethane: −14.6 minutes.

Standard wet chemistry types of analytical procedures were performed on the lighter (upper) aqueous phase (containing water and secondary products) of the reaction mixture, collected during the process.

Preparation of Bromopicrin

General Procedure:
A mixture of nitromethane (NM) and bromine is prepared at room temperature (RT) in a first batch-type reactor. This mixture is stable at room temperature for at least 7 days. In a second batch-type reactor, an aqueous solution of alkaline base (e.g., sodium hydroxide) is prepared. A stream of the NM/bromine mixture and a stream of the aqueous-alkaline-base are then simultaneously transferred into a continuous-type reactor by means of calibrated peristaltic pumps, so as to form a yellow-green reaction mixture. The pH of the reaction mixture is maintained at about 10-12 and the temperature is varied between 40° C. and 80° C. The reaction is fast and exothermic and the yield is almost quantitative.

Optionally and preferably, the reaction mixture or a portion thereof is then transferred into a secondary reactor where the reaction is completed while the mixture is being cooled to room temperature. Then, the reaction mixture is passed into a separating funnel, or a reparatory system composed of one or two separating funnels, where the phases are separated by means of collecting the lower organic phase containing the bromopicrin (d from about 2.75 grams/cm$^3$ to about 2.78 grams/cm$^3$). The upper aqueous phase (d about 1.5 grams/cm$^3$) containing the sodium bromide, oxidants and traces of organic material, is also collected.

FIG. 1 presents a generalized flow block diagram of the continuous process described herein.

Exemplary Experiments:

In an exemplary experiment (Run 38745-44), NM/Br$_2$ mixture and aqueous 27% NaOH solution were simultaneously introduced into a 1 L reactor, at a rate of about 6 ml/minute and about 10 ml/minute, respectively, and the mechanical stirrer was operated at 400 rpm. The set point of the cooling solution in the Lauda temperature controller was set to 23° C.-27° C. The reaction was fast and the bromine color disappeared immediately. The temperature in the reactor rose to 40° C. and remained at 40±2° C. The pH of the reaction mixture was checked from time to time and was in the range 10-12. After about one hour of feeding, the reaction mixture began to flow into a secondary, stirred round-bottom flask, and from there, after about 8 minutes, into the separating funnel. The temperature in the secondary flask was maintained at about 20° C. by external cooling and the pH was about 11.

It should be noted that the pH in the first chemical reactor is controllable, and can be adjusted by manipulating the addition rate of the aqueous solution of the alkaline substance (NaOH).

The set point of the cooling solution can also be manipulated and in some experiments was set, for example, to 55-56° C. In general, the set point of the cooling solution is determined according to the residence time and/or the desired temperature in the reactor. The process was carried out continuously for about 6 hours, during which 5520 grams of a nitromethane in Br$_2$ mixture (600 grams of nitromethane in 4920 grams of bromine) and 4626 grams of a 27% NaOH aqueous solution were fed in. After collecting all the solutions from the separating funnel, the reactor and the round-bottom flask, 2845 grams BP and 7284 grams of an aqueous solution were obtained.

FIG. 2 presents a flow block diagram of the continuous process described herein (for sample 38745-44).

Two additional representative experiments are displayed as flow block diagrams in FIGS. 3 and 4, respectively.

Experimental Results

Table 1 below presents the reaction conditions and product analysis of several exemplary processes that followed the general procedure described hereinabove.

As shown in Table 1, in all processes, the purity of the crude bromopicrin collected as the organic phase, was higher than 99% by weight, as determined by quantitative GC, and the process yield reached 96-98%, based on nitromethane. The reaction is exothermic and very fast and is almost completed in the first reactor into which the reagents are fed.

The molar ratio between the bromine and the nitromethane used as starting materials was almost stoichiometric (from 3.0:1 to 3.1:1) and hardly any excess of bromine was used. It has been shown that at a bromine:nitromethane molar ratio of 3.05 (equivalent to a bromine:nitromethane weight ratio of 8.0), the selectivity of the reaction is above 99%.

In all processes, a 26-27% NaOH solution was used, and the molar ratio between the sodium hydroxide and the nitromethane was from 3.0:1 to 3.2:1.

Furthermore, the reproducibility of the continuous process for the production of BP on a laboratory scale has been demonstrated. Thus, for example, the experiment displayed in FIG. 4 (Run No. 38846-7), has been carried out continuously over 30 hours, while the high yield and purity of the product was maintained, demonstrating the reproducibility of the process.

The temperature within the first reactor varied between 38° C. and 80° C.

The residence time in the main reactor ($t_1$) varied between 30 minutes and 4 hours, showing that even during a very short residence time, the final yield was very high (>98%).

As can be seen in Table 1 (see, samples 41, 42, 44, 46, 47 and 50), bromopicrin was obtained at a throughput of between 300 grams/hour·liter to 1,000 grams/hour·liter, indicating, for example, a throughput of BP in an 8 m$^3$ (8,000 liter) reactor in the continuous process, of from about 2.4 tons/hour, in a process that involves a two-hours residence time, and even up to 8 tons/hour! provided that the heat evolution is effectively controlled.

TABLE 1

| Sample No. | Br$_2$ grams | NM Grams | Br$_2$/NM molar ratio | NaOH grams | NaOH % weight | NaOH/NM molar ratio | addition time hours | $T_R$ ° C. | $t_1$ hours |
| --- | --- | --- | --- | --- | --- | --- | --- | --- | --- |
| 41 | 1640 | 200 | 3.13 | 1548 | 26.5 | 3.13 | 2.3 | 38 ± 2 | 0.6 |
| 42 | 3280 | 400 | 3.13 | 3152 | 27.0 | 3.24 | 4 | 38 ± 2 | 0.5 |
| 44 | 4920 | 600 | 3.13 | 4626 | 27.0 | 3.18 | 6 | 40 ± 2 | 1.1 |
| 46 | 4920 | 610.5 | 3.07 | 4756 | 26.7 | 3.17 | 8.3 | 40 ± 2 | 1.5 |
| 47 | 4800 | 610.4 | 3.00 | 4536 | 26.7 | 3.03 | 9 | 40 ± 2 | 1.7 |
| 50 | 4893 | 610.4 | 3.06 | 4575 | 27.3 | 3.12 | 7.25 | 60 ± 2 + 80 ± 2 | 1.4 |
| 7 | 12,384 | 1548 | 3.05 | 11,598 | 27.2 | 3.11 | 30 | 60 ± 2 | 2.3 |

TABLE 1-continued

| Sample No. | $T_R(2)$ °C | pH(2) | $t_2$ minutes | BP throughput grams | grams/ hour | grams/ hour/l* | BP yield % |
|---|---|---|---|---|---|---|---|
| 41 | 25 ± 5 | 9.0-9.2 | 8.8 | 938 | 408 | 850 | 96.1 |
| 42 | 25 ± 5 | 9.6-9.9 | 7.5 | 1919 | 480 | 1000 | 98.2 |
| 44 | 20 ± 5 | 9.4-11.9 | 7.6 | 2845 | 474 | 439 | 97.1 |
| 46 | 20 ± 5 | 9.7-10.3 | 10.2 | 2892 | 348 | 322 | 97.0 |
| 47 | 22 ± 7 | 9.9-10.4 | 11.4 | 2908 | 323 | 299 | 97.6 |
| 50 | 24 ± 5 | 9.6-10.3 | 9.2 | 2883 | 398 | 369 | 96.7 |
| 7 | 30 ± 5 | 10.5-11.5 | 15.0 | 7398 | 247 | 228 | 97.9 |

NM = nitromethane, BP = bromopicrin, Grams solution indicates the weight of the NaOH aqueous solution in grams; % weight NaOH indicates the NaOH weight concentration in the aqueous solution stream, addition time indicates the time over which both streams of reactants (NaOH aqueous solution, NM in bromine) entered the first reactor, $T_R$ = temperature in the first reaction reactor, $t_1$ indicates the residence time in the first reactor, $T_R(2)$ = temperature in the second reaction reactor, pH(2) = pH in the second reaction reactor, $t_2$ indicates the residence time in the second reactor. Yield is relative to the NM.
*Reactor volume in Sample Nos. 41 and 42 was 0.48 liter and in Sample Nos. 44, 46, 37, 50 and 7 1.08 liter.

Composition analysis of the collected lighter (upper) aqueous phase (containing water and secondary products) of some samples of the reaction mixture, before and after chemical treatment, is listed in Table 2 below.

TABLE 2

| Sample no. | Weight of aqueous phase grams | Oxidants (as $BrO^-$) Weight % | NaBr Weight % | TOC ppm | pH |
|---|---|---|---|---|---|
| 41 | 2442 | 1.7 | 45.2 | 25 | 9.0 |
| 42 | 4906 | 1.6 | 45.0 | 28 | 9.5 |
| 44 | 7284 | 1.7 | 45.1 | 32 | 11.6 |
| 46 | 7301 | 1.2 | 45.0 | 106 | 12.6 |
| 47 | 6956 | 0.3 | 45.5 | 30 | 12.5 |
| 50 | 7124 | 1.0 | 45.2 | 22 | 11.9 |
| 7 | 17946 | 0.8 | 44.3 | 40 | 11.7 |

TOC = total organic carbon. ppm = parts per million.

As can be seen in Table 2, the aqueous phase typically contains about 45% NaBr, between 0.4 and 2.1% oxidants (as NaBrO) and traces of organic materials. The total organic carbon (TOC) varied between 22 ppm to about 106 ppm.

The concentration of the aqueous NaOH affects the concentration of both NaBr and NaBrO salts in the aqueous phase. It has been shown that using aqueous NaOH at about 27% concentration results in an aqueous solution containing about 45% salts, which do not precipitate in the aqueous phase at room temperature (RT) conditions.

The average consumption of the main raw materials for the preparation of crude bromopicrin by the continuous process is summarized in Table 3 below.

TABLE 3

| Raw material | MW | Consumption, kg/kg Theoretical | Consumption, kg/kg Practical | Yield of BP, % based on: |
|---|---|---|---|---|
| Nitromethane | 61 | 0.205 | 0.209 | 97.9 |
| Bromine* | 160 | 1.611 | 1.674 | 96.2 |
| NaOH (100%) | 40 | 0.403 | 0.426 | 94.6 |
| Bromopicrin | 298 | | | |

*when no re-generation of bromine is effected

It is appreciated that certain aspects and characteristics of the invention, which are, for clarity, described in the context of separate embodiments, may also be provided in combination in a single embodiment. Conversely, various aspects and characteristics of the invention, which are, for brevity, described in the context of a single embodiment, may also be provided separately or in any suitable sub-combination.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A process of preparing bromopicrin, the process comprising:
    transferring a continuous flow of a first mixture and a continuous flow of a second mixture into a first reactor, said first mixture containing nitromethane and bromine and said second mixture containing an aqueous solution of an alkaline substance, wherein said first reactor is maintained at a temperature that ranges from about 40° C. to about 80° C., to thereby obtain a reaction mixture which comprises bromopicrin in said first reactor; and
    collecting the bromopicrin from said reaction mixture, thereby preparing bromopicrin.

2. The process of claim 1, wherein said first mixture and said second mixture are transferred, via said continuous flow, into said first reactor simultaneously.

3. The process of claim 1, wherein said process is performed such that said reaction mixture is substantially absent of an organic solvent.

4. The process of claim 1, wherein said first mixture is prepared by mixing nitromethane and bromine at a temperature that ranges from about 10° C. to about 50° C.

5. The process of claim 4, wherein said temperature ranges from about 20° C. to about 25° C.

6. The process of claim 1, wherein a molar ratio of said bromine and said nitromethane in said first mixture ranges from about 3 to about 4.

7. The process of claim 6, wherein said ratio ranges from about 3 to about 3.1.

8. The process of claim 1, wherein said alkaline substance is selected from the group consisting of metal alkali hydroxides, alkaline earth hydroxides, and combinations thereof.

9. The process of claim 8, wherein said metal alkali hydroxide is selected from the group consisting of lithium hydroxide, sodium hydroxide, potassium hydroxide and combinations thereof.

10. The process of claim 8, wherein said metal alkali hydroxide is selected from the group consisting of sodium hydroxide, potassium hydroxide and a combination thereof.

11. The process of claim 8, wherein said alkaline substance is sodium hydroxide.

12. The process of claim 1, wherein a concentration of said alkaline substance in said aqueous solution of said second mixture ranges from about 5 weight percents to about 40 weight percents of the total weight of said aqueous solution weight.

13. The process of claim 12, wherein a concentration of said alkaline substance in said aqueous solution of said second mixture ranges from about 20 weight percents to about 35 weight percents of the total weight of said aqueous solution weight.

14. The process of claim 13, wherein said concentration ranges from about 26 weight percents to about 27 weight percents of the total weight of said aqueous solution weight.

15. The process of claim 1, wherein a residence time of said reaction mixture in said first reactor ranges from about 0.3 hours to about 6 hours.

16. The process of claim 15, wherein said residence time ranges from about 0.5 hours to about 4 hours.

17. The process of claim 1, further comprising, prior to collecting said bromopicrin, transferring said reaction mixture from said first reactor to a second reactor.

18. The process of claim 17, wherein said second reactor is maintained at a temperature that ranges from about 15° C. to about 30° C.

19. The process of claim 18, wherein said temperature ranges from about 20° C. to about 25° C.

20. The process of claim 1, further comprising, prior to said collecting the bromopicrin, cooling said reaction mixture.

21. The process of claim 1, further comprising, subsequent to collecting said bromopicrin, collecting an aqueous phase from said reaction mixture.

22. The process of claim 21, further comprising chemically treating said aqueous phase, to thereby provide a treated form of said aqueous phase.

23. The process of claim 22, wherein said chemically treating said aqueous phase comprises regeneration of bromine and/or sodium bromide.

24. The process of claim 1, wherein the bromopicrin is obtained in a chemical yield equal to or higher than 90 weight percents, relative to nitromethane.

25. The process of claim 24, wherein the bromopicrin is obtained in a chemical yield equal to or higher than 95 weight percents, relative to nitromethane.

26. The process of claim 24, wherein the bromopicrin is obtained in a chemical yield equal to or higher than 98 weight percents, relative to nitromethane.

27. The process of claim 1, wherein the bromopicrin has a purity equal to or higher than 99 weight percents.

\* \* \* \* \*